United States Patent
Paschalis

(10) Patent No.: US 11,480,740 B2
(45) Date of Patent: Oct. 25, 2022

(54) OPTICAL FIBER COUPLING APPARATUSES, SYSTEMS, AND METHODS

(71) Applicant: Massachusetts Eye and Ear Infirmary, Boston, MA (US)

(72) Inventor: Eleftherios Ilios Paschalis, Quincy, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 327 days.

(21) Appl. No.: 16/769,748

(22) PCT Filed: Dec. 4, 2018

(86) PCT No.: PCT/US2018/063864
§ 371 (c)(1),
(2) Date: Jun. 4, 2020

(87) PCT Pub. No.: WO2019/113083
PCT Pub. Date: Jun. 13, 2019

(65) Prior Publication Data
US 2020/0379189 A1     Dec. 3, 2020

Related U.S. Application Data

(60) Provisional application No. 62/594,939, filed on Dec. 5, 2017.

(51) Int. Cl.
| | | |
|---|---|---|
| *G02B 6/38* | (2006.01) | |
| *A61B 3/16* | (2006.01) | |
| *A61F 2/14* | (2006.01) | |
| *A61F 2/16* | (2006.01) | |

(52) U.S. Cl.
CPC ............. *G02B 6/3886* (2013.01); *A61B 3/16* (2013.01); *A61F 2/142* (2013.01); *A61F 2/16* (2013.01); *G02B 6/382* (2013.01); *A61F 2210/009* (2013.01)

(58) Field of Classification Search
None
See application file for complete search history.

(56) References Cited

U.S. PATENT DOCUMENTS

| | | | |
|---|---|---|---|
| 4,236,784 A | | 12/1980 | Palmer |
| 4,368,430 A | * | 1/1983 | Dale .................... G01R 33/038 505/845 |
| 5,247,172 A | | 9/1993 | Riemer |
| 5,295,212 A | | 3/1994 | Morton et al. |
| 9,236,942 B1 | | 1/2016 | Roberds et al. |
| 9,389,371 B2 | | 7/2016 | Butler et al. |
| 2006/0287662 A1 | | 12/2006 | Berry et al. |
| 2014/0120746 A1 | | 5/2014 | Persion et al. |
| 2017/0035275 A1 | | 2/2017 | Yajima et al. |

OTHER PUBLICATIONS

PCT International Preliminary Report on Patentability in International Appln. PCT/US2018/063864, dated Jun. 9, 2020, 7 pages.
PCT International Search Report and Written Opinion in International Appln. No. PCT/US2018/063864, dated Feb. 21, 2019, 14 pages.

* cited by examiner

*Primary Examiner* — Chris H Chu
(74) *Attorney, Agent, or Firm* — Fish & Richardson P.C.

(57) ABSTRACT

The present disclosure relates to optical fiber coupling systems and methods of coupling optical fibers across and with a magnetic field.

26 Claims, 5 Drawing Sheets

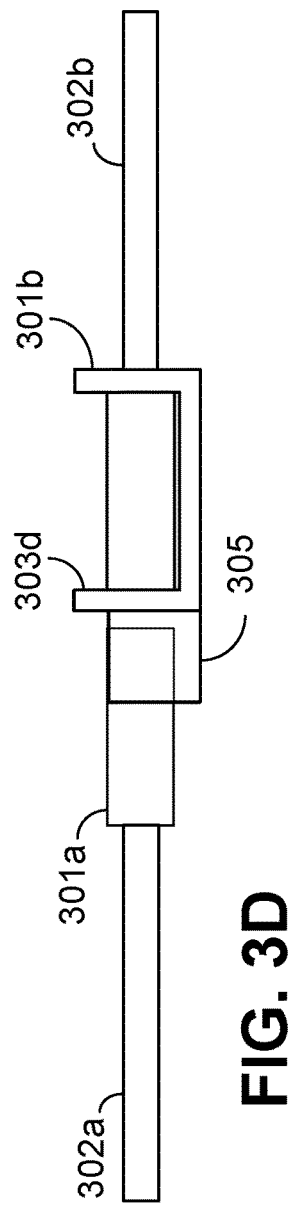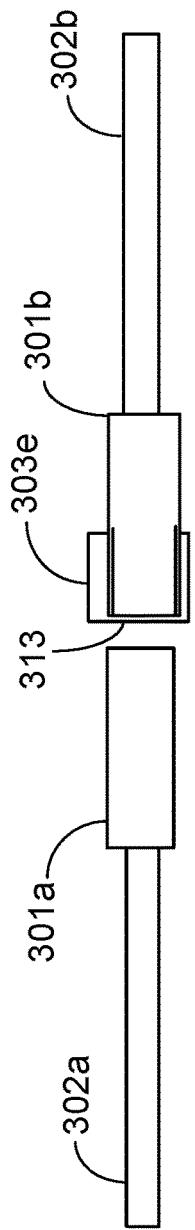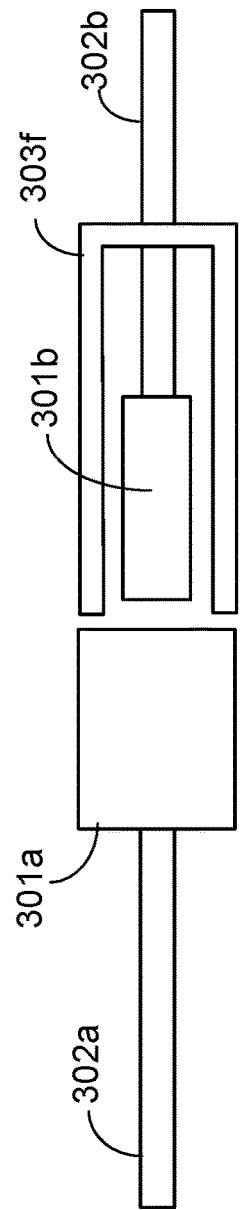

OPTICAL FIBER COUPLING APPARATUSES, SYSTEMS, AND METHODS

RELATED APPLICATIONS

The present application is a national stage application of PCT/US2018/063864, filed on Dec. 4, 2018, which claims priority to U.S. Provisional Patent Application No. 62/594,939, filed Dec. 5, 2017, entitled, "OPTICAL FIBER COUPLING APPARATUSES, SYSTEMS, AND METHODS," which application is incorporated herein by reference in its entirety.

TECHNICAL FIELD

The present application relates generally to the field of optical fiber coupling systems.

BACKGROUND

Currently coupling of two fibers requires splicing and joining the fibers using an electro voltaic arc or laser heat. Also, connector components are available to couple two fibers, but do not allow freedom of movement of the fibers if needed. The lack of freedom of movement of optical fibers disadvantageously impacts how and where the optical fibers can be used and implemented. For example, emerging generations of 3-D optical coherent tomographs (OCT) employ a rotating fiber optic camera on the one end, and a fixe fiber optic coupled detector/analyzer on the other end. Many times, these cameras need to rotate at high angular speeds to increase image quality, which makes fiber alignment very difficult. This process generates vibrations, centrifugal forces, and tremors that misalign the optical fibers, particularly at elevated angular speeds. Certain implantable optical sensors employ in vivo coupling with an interrogation fiber. Connectorizing such devices is not always feasible advantageous.

SUMMARY

The inventor has discovered that magnetic systems can be effectively employed to couple optical fibers at a distance while effectively permitting transmission of optical signals across a gap from one optical fiber to another. Accordingly, various embodiments disclosed herein provide apparatuses, systems, and methods for non-contact coupling and/or aligning optical fibers with a magnetic field across a gap. The embodiments disclosed herein use air and/or other refractive mediums as an interface between two optical fibers (gas, liquid, gel, etc). The embodiments permit two separate fibers to have freedom of movement in one or more directions and rapidly re-align after displacement. The apparatuses, systems, and methods may be applied to fiber optic communication of any sort, and in particular, fiber optic communication through the cornea, in vibrating environments where physical contact could lead to undue wear and tear, and in laboratory setting for rapid fiber coupling during experiments.

Various embodiments provide optical fiber coupling systems. The systems include a first optical fiber comprising a first magnetic collar attached coaxially to a proximal end of the first optical fiber. The systems include a second optical fiber comprising a second magnetic collar attached coaxially to a proximal end of the second optical fiber. The second magnetic collar is attached to the proximal end of the second fiber so as to have a polarity at a coupling end of the second magnetic collar adjacent a terminus of the proximal end of the second optical fiber, which polarity is opposite a polarity of a coupling end of the first magnetic collar adjacent to a terminus of the proximal end of the first optical fiber. The systems include a spacer attached to at least one of the first optical fiber and the first magnetic collar. The spacer protrudes beyond the first magnetic collar with respect to the proximal end of the first optical fiber so as to be positioned between the coupling end of first magnetic collar and the coupling end of the second magnetic collar upon magnetic engagement of a magnetic field of the coupling end of the first magnetic collar with a magnetic field of the coupling end of the second magnetic collar. The spacer is configured to maintain a gap between the first magnetic collar and the second magnetic collar across which the magnetic fields engage one another. The second magnetic collar abuts the spacer. The spacer is configured to allow an optical signal to pass from the first optical fiber to the second optical fiber.

In some implementations, the spacer includes an opening through which the optical signal can pass.

In some implementations, the opening has a cross section that is smaller than a cross section of the coupling end of second magnetic collar.

In some implementations, the opening has a cross section that is smaller than a cross section of the coupling end of the first magnetic collar and the coupling end of the second magnetic collar.

In some implementations, the spacer has a tapered cross section.

In some implementations, the spacer is composed of a non-magnetic material.

In some implementations, the spacer is configured as a concentric collar.

In some implementations, the first magnetic collar and the second magnetic collar have distinct cross sectional areas at the respective coupling ends.

In some implementations, the spacer includes a recessed region configured for nesting the second magnetic collar.

In some implementations, the spacer is configured to maintain the gap at a distance in the range of, for example, 1 nm-1000 microns.

In some implementations, the spacer is configured to maintain the gap at a distance in the range of 2-500 microns.

In some implementations, the spacer is configured to maintain the gap at a distance of 1 mm.

In some implementations, the spacer is configured to coaxially align the coupling end of the first magnetic collar with the coupling end of the second magnetic collar.

In some implementations, a distal end of the first optical fiber extends from the first magnetic collar to a light source.

In some implementations, a distal end of the second optical fiber extends from the second magnetic collar to into a keratoprosthesis.

In some implementations, a distal end of the second optical fiber extends from the second magnetic collar to into an intraocular lens.

In some implementations, the system includes a pressure sensor positioned on the coupling end of the second magnetic collar.

Various embodiments provide methods of coupling optical fibers for communicatively transmitting optical signals. The methods include coaxially attaching a first magnetic collar to a proximal end of a first optical fiber. The methods include coaxially attaching a second magnetic collar to a proximal end of a second optical fiber. The second magnetic collar is attached to the proximal end of the second fiber so as to have a polarity at a coupling end of the second magnetic collar adjacent a terminus of the proximal end of the second optical fiber, which polarity is opposite a polarity of a coupling end of the first magnetic collar adjacent to a terminus of the proximal end of the first optical fiber. The methods include attaching a spacer to at least one of the first optical fiber and the first magnetic collar such that the spacer protrudes beyond the first magnetic collar with respect to the proximal end of the first optical fiber. The methods include positioning the first magnetic collar with respect to the second magnetic collar so that the spacer is positioned between the coupling end of the first magnetic collar and the coupling end of the second magnetic collar, so that the second magnetic collar abuts the spacer, so that a magnetic field of the coupling end of the second magnetic collar engages a magnetic field of the coupling end of the first magnetic collar, whereby the spacer maintains a gap between the first magnetic collar and the second magnetic collar across which the magnetic fields engage one another, and so that an optical signal is configured to pass from the first optical fiber to the second optical fiber.

In some implementations, the methods include transmitting the optical signal from the first optical fiber to the second optical fiber through the spacer and across the gap.

In some implementations, the methods include rotating the first optical fiber with respect to the second optical fiber.

In some implementations, the methods include positioning comprising coaxially aligning the terminus of the first optical fiber with the terminus of the second optical fiber.

In some implementations, the first optical fiber is positioned with respect to the second optical fiber so that the gap is at a distance in the range of 1 nm-1000 microns or more.

In some implementations, the methods are employed to facilitate the medical use of µOCT.

Various embodiments provide methods of coupling optical fibers for communicatively transmitting optical signals. The methods include coaxially attaching a first magnetic collar to a proximal end of a first optical fiber. The methods include coaxially attaching a second magnetic collar to a proximal end of a second optical fiber. The second magnetic collar is attached to the proximal end of the second fiber so as to have a polarity at a coupling end of the second magnetic collar adjacent a terminus of the proximal end of the second optical fiber, which polarity is opposite a polarity of a coupling end of the first magnetic collar adjacent to a terminus of the proximal end of the first optical fiber. The methods include positioning the first magnetic collar with respect to the second magnetic collar so that a gap is between the coupling end of the first magnetic collar and the coupling end of the second magnetic collar, so that a magnetic field of the coupling end of the second magnetic collar engages a magnetic field of the coupling end of the first magnetic collar. The methods include causing an optical signal to be passed from the first optical fiber to the second optical fiber across the gap.

In some implementations, the first magnetic collar and the first optical fiber are attached to a movable slit lamp or other hand-held, wearable or fixed to the ground ocular examination device. The first optical fiber is movable with respect to the slit lamp. The slit lamp is configured to move with respect to the second magnetic collar to engage the magnetic field of the coupling end of the second magnetic collar with the magnetic field of the coupling end of the first magnetic collar with the gap positioned therebetween during transmission of the optical signal from the first optical fiber to the second optical fiber. The slit lamp may include a spacer.

In some implementations, the first optical fiber and the second optical fiber are positioned within a chamber comprising a refractive index matching liquid. The method may include rotating at least one of the first optical fiber and the second optical fiber in the chamber.

All combinations of the foregoing concepts and additional concepts discussed in greater detail below (provided such concepts are not mutually inconsistent) are part of the inventive subject matter disclosed herein. In particular, all combinations of claimed subject matter appearing at the end of this disclosure are part of the inventive subject matter disclosed herein. Terminology explicitly employed herein that also may appear in any disclosure incorporated by reference should be accorded a meaning most consistent with the particular concepts disclosed herein.

For the purpose of this disclosure, the term "coupled" means the joining of the optical signal of two optical fiber members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another or suspended in an arrangement. Such joining may be permanent in nature or may be removable or releasable in nature.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages will be apparent from the following detailed description, and from the claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 3A-3H illustrate examples of a spacer devices coupled to an optical fiber as described herein.

The features and advantages of the inventive concepts disclosed herein will become more apparent from the detailed description set forth below when taken in conjunction with the drawings.

DETAILED DESCRIPTION

Following below are more detailed descriptions of various concepts related to, and exemplary embodiments of, inventive systems, methods, and components related to optical fiber coupling systems.

Figure 1:
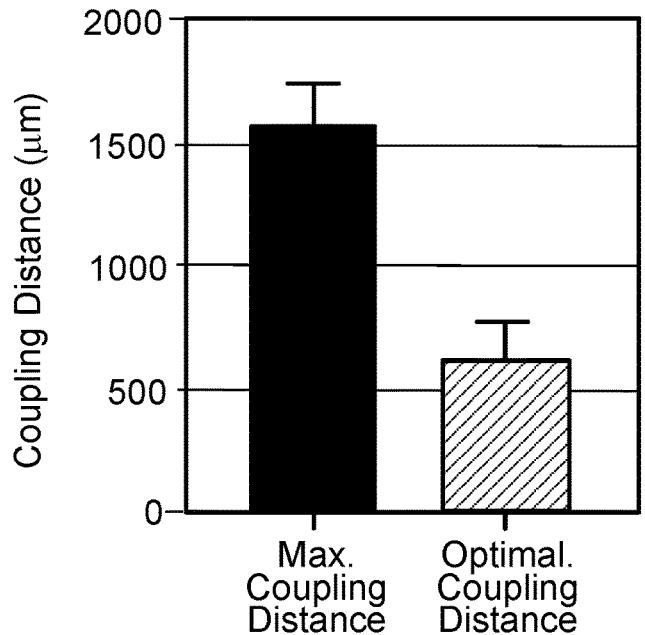
FIG. 1 illustrates a graph of coupling distances of optical fibers as described herein.

FIG. 1 illustrates a graph of optical fibers including magnetic collars as described herein. Implementations of the present invention advantageously improve the efficiency of non-contact optical fiber coupling, since they provide continuous auto-alignment of the optical fibers. In particular, FIG. 1 shows example distances between two vibrating fibers where none contact coupling can be performed and optimized for optical transmission between the non-contacting optical fibers. Embodiments of the coupling systems disclosed herein can be employed for a step-index monomode optical fibers and for step-index or gradient-index multimode optical fibers.

Coupling of light does not necessarily require physical contact. Physical contact can be achieved by splicing fibers, but this is not practical in certain instances. Instead, according to embodiments disclosed herein connectors are implemented that bring two optical fibers very close, but an air gap is present at the interface, particularly in angled polished fibers. The distance between the optical fibers dictates the loss of light, especially when the refractive index of air is lower than that of the fiber. However, by using lensed fibers (tapered), anti-reflective (AR) coatings and/or matching index media (liquid, gas, or gel), high coupling efficiency can be achieved even at large distances. Such arrangements yield high efficiency coupling of light, when the fibers are properly aligned. Certain fiber optic applications, including some employing sensors, have power control that can compensate for such losses.

Figure 2:
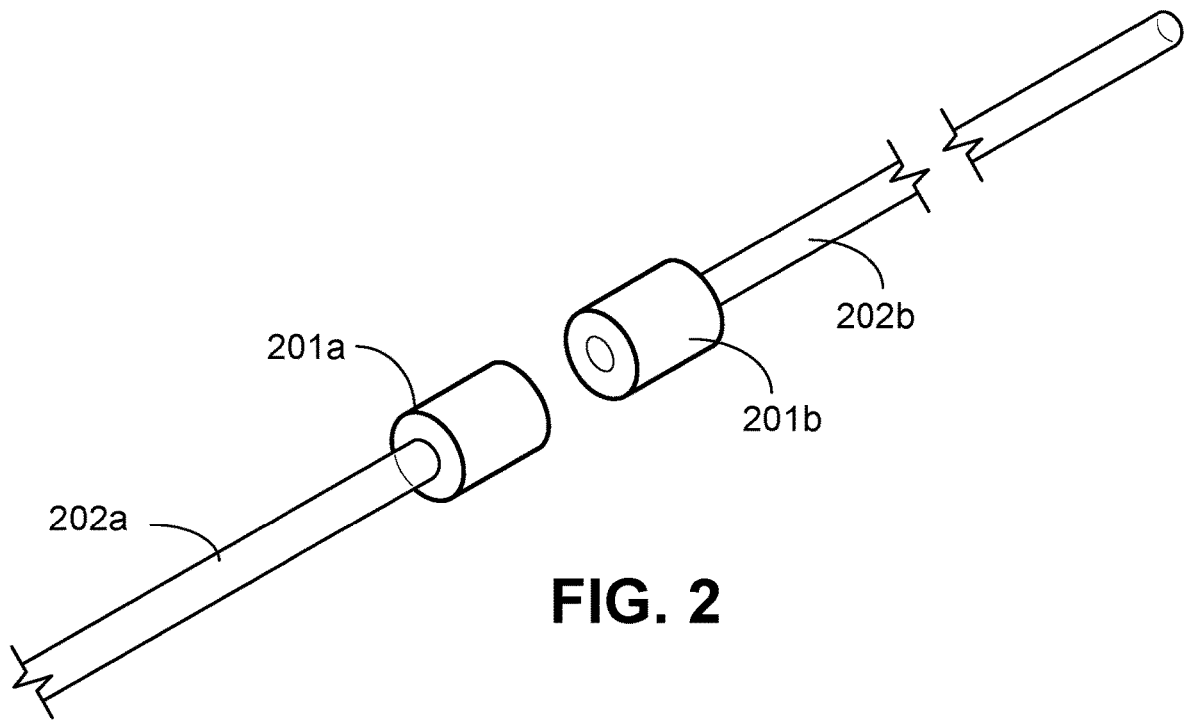
FIG. 2 illustrates optical fibers including magnetic collars as described herein.

FIG. 2 illustrates optical fibers including magnetic collars as described herein. Optical fiber coupling systems include a first magnetic collar 201a attached coaxially to a proximal end of a first optical fiber 202a. The systems include a second magnetic collar 201b attached coaxially to a proximal end of a second optical fiber 202b. The second magnetic collar 201b is attached to the proximal end of the second fiber 202b so as to have a polarity at a coupling end of the second magnetic collar 201a adjacent a terminus of the proximal end of the second optical fiber 202b, which polarity is opposite a polarity of a coupling end of the first magnetic collar 201a adjacent to a terminus of the proximal end of the first optical fiber 202b. Accordingly, the magnetic collars 201a and 201b are positioned on the respective optical fibers 202a and 202b such that a north pole of one magnetic collar is adjacent a south pole of the other magnetic collar as demonstrated in FIG. 2.

In certain implementations the magnetic collars 201a and 201b comprise neodymium ring-shaped micro magnets (e.g. ID: 145 μm×OD:350 μm×L:500 μm) that are fitted to the tip of the two fibers 202a and 202b, having opposite magnetization (attractive force). Using magnetic attraction, the two fibers 202a and 202b are auto aligned as the magnetic collars 201a and 201b come closer together and maintain alignment even at high vibrations amplitudes and frequencies or even if one or both are rotating. The two fibers 202a and 202b can pull closely together, if needed, thereby performing a reversible coupling arrangement. This ability is important for acquiring intraocular pressure measurements, for example with a keratoprosthesis device including an integrated fiber optic pressure sensor, as discussed in further detail in connection with FIGS. 4A and 4B. This is also important for other implantable fiber-optic biosensors where the interrogation fiber cannot be permanently fixed to the individual and needs to perform in vivo rapid and precise alignment with the implanted fiber sensor to acquire data.

Precautions are taken to avoid collision of the two fibers 202a and 202b via a spacing component as demonstrated further in FIGS. 3A-3H. In certain embodiments, the magnetic collar provides spacing via the optical fiber being recessed or positioned within the magnetic collar so that the end of the fiber is spaced a few micrometers from the end of the magnetic collar. Various embodiments of this invention can also be used in the fiber optic industry as a standalone coupler arrangement or in conjunction with more sophisticated coupling systems that contain roulemans as those used in the new generation of 3-D OCTs. Embodiments of the coupling systems can dampen 3-D vibrations and maintain fiber coupling even at vibration amplitude of 100 times the fiber-optic diameter and with a separation distance between the fibers of more than 500 micrometers (see FIG. 2). Coupling efficiency can be enhanced by creating a liquid tight chamber around the two optical fibers and suspending the fibers in refractive index matched liquid (e.g. oil). These systems provide a way to couple fibers at a distance. This can be implemented, for example, in in vivo fiber optic measurements using optical sensors or guiding light in photo medicine. Thus, these systems can substantially improve the efficiency and image quality of new generation rotating 3-D OCTs, perform in vivo and in vitro measurements of fiber optic sensors or used in conjunction with fiber-optic guided light activated drugs implanted in the body. Precise light guides can be provided via coupling system embodiments disclosed herein. Other applications are possible, for example in the field of ophthalmology.

FIGS. 3A-3E illustrate examples of a spacer devices coupled to an optical fiber as described herein. Optical fiber coupling systems includes a first magnetic collar 301a attached coaxially to a proximal end of a first optical fiber 302a. The systems include a second magnetic collar 301b attached coaxially to a proximal end of a second optical fiber 302b. The systems include a spacer 303a attached to the optical fiber 302b and/or the magnetic collar 301b. The spacer 303a protrudes slightly beyond the magnetic collar 301b with respect to the proximal end 310 of the optical fiber 302b so as to be positioned between the coupling end of magnetic collar 301b and the coupling end of the magnetic collar 301a during magnetic engagement of a magnetic field of the coupling end of the magnetic collar 301b with a magnetic field of the coupling end of the magnetic collar 301a. The spacer 303a is configured to maintain a gap between the magnetic collar 301b and the magnetic collar 301a across which the magnetic fields engage one another. The magnetic collar 301a abuts the spacer 303a. The spacer 303a is configured to allow an optical signal to pass from the first optical fiber 302b to the optical fiber 302a, between an opening 311 in the spacer 303a.

Figure 3A:
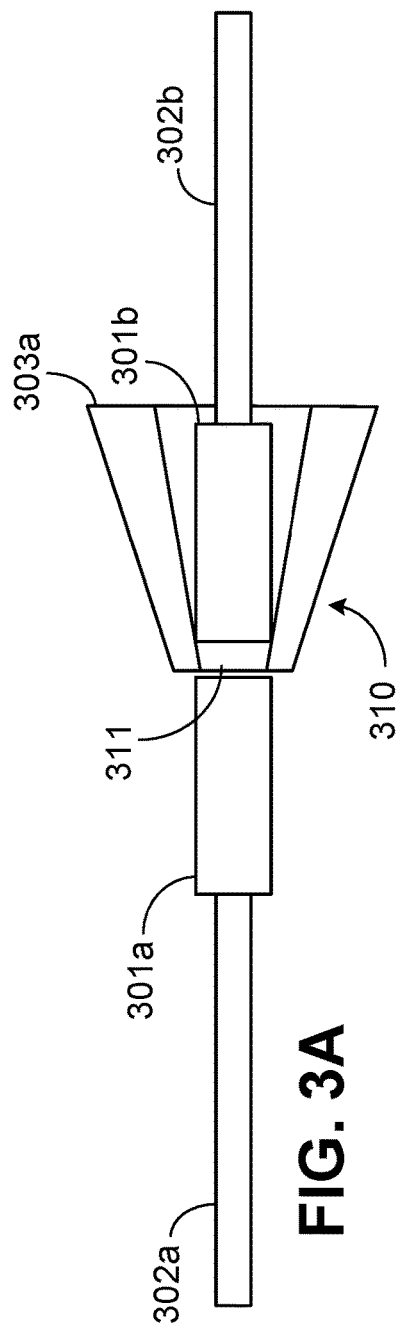
Figure 3B:
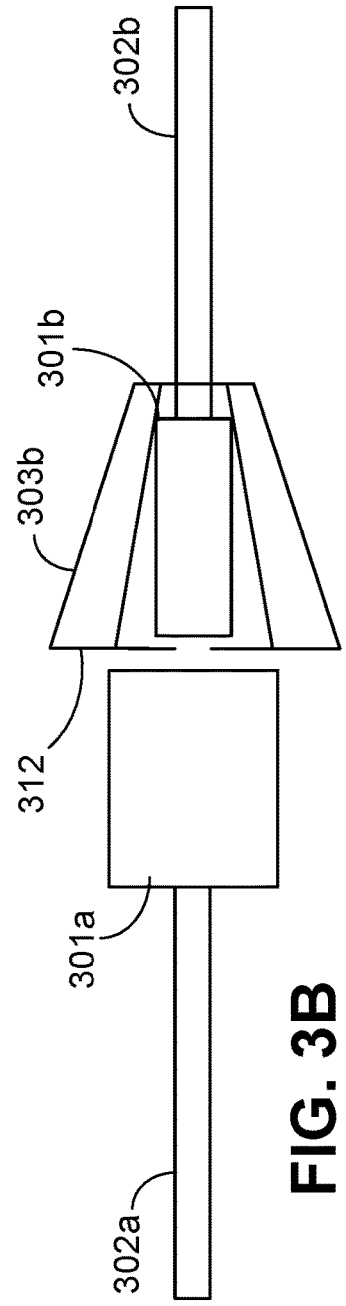

As demonstrated in FIG. 3B, in certain embodiments, the magnetic collar 301a can have a distinct size with respect to the magnetic collar 301b. The magnetic collar 301a may have a size that is configured to prevent it from passing the peripheral portion 312 of spacer 303b. Spacer 303b can be inverted on magnetic collar 301b in certain embodiments.

Figure 3C:
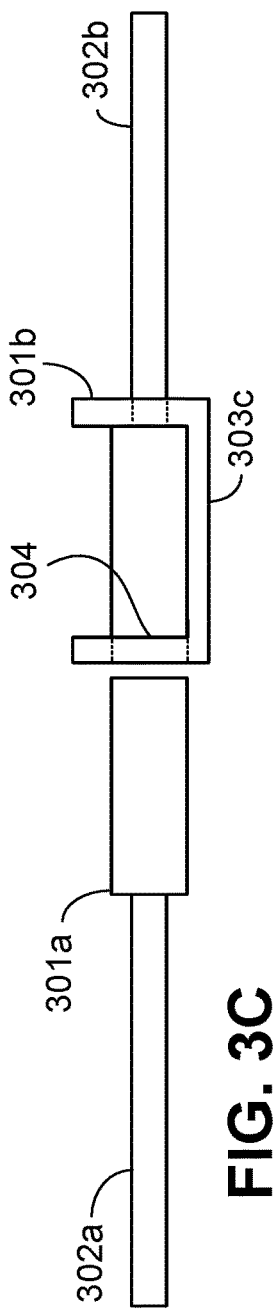

While spacers 303a and 303b have a tapered geometry, the spacer can have a non-tapered geometry such as spacer 303c shown in FIG. 3C. The spacer 303c includes an opening 304 through which light can pass.

As illustrated in FIG. 3D, a spacer 303d can include a recess or seat 305 for nesting the magnetic collar 301a. The magnetic collar 301a can be free to rotate in the recess 305.

Similarly, the magnetic collar 30b can be free to rotate in the spacer 303d (as well as 303a-303e).

As illustrated in FIG. 3E, a spacer 303e can be provided that is configured as a cap positioned on the end of magnetic collar 301b with an opening 313 through which light can pass. The magnetic collar 301a can directly contact the spacer 303e. The spacer can have a thickness beyond the edge of collar 301b that permits the magnetic fields to engage one another and that permits the optical signal to be effectively passed between the optical fibers 302a and 302b.

As demonstrated in FIG. 3F, in certain embodiments, the magnetic collar 301a can have a distinct size with respect to the magnetic collar 301b. The magnetic collar 301a may have a size that is configured to prevent it from passing the peripheral portion of spacer 303f Spacer 303f can be coupled to a device, such as a slit lamp device. The optical fiber 302b can be movable with respect to the spacer 303f (e.g. rotatable in an opening in the spacer or slidable along a co-axis through the opening in the spacer).

Figure 3G:
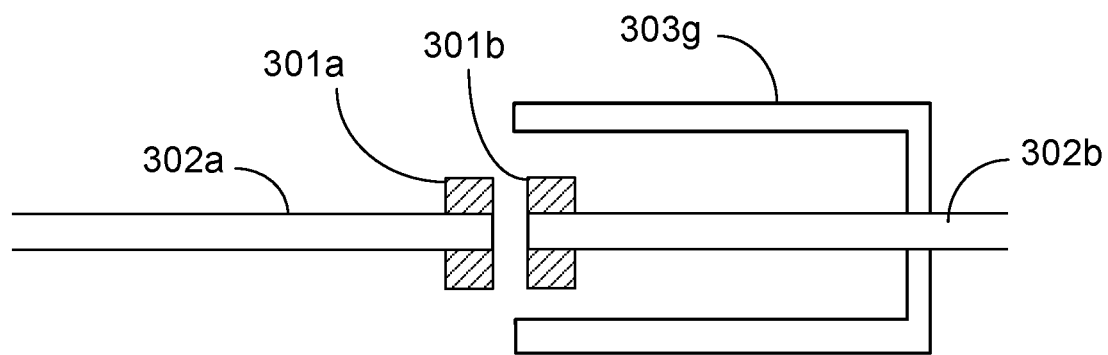
Figure 3H:
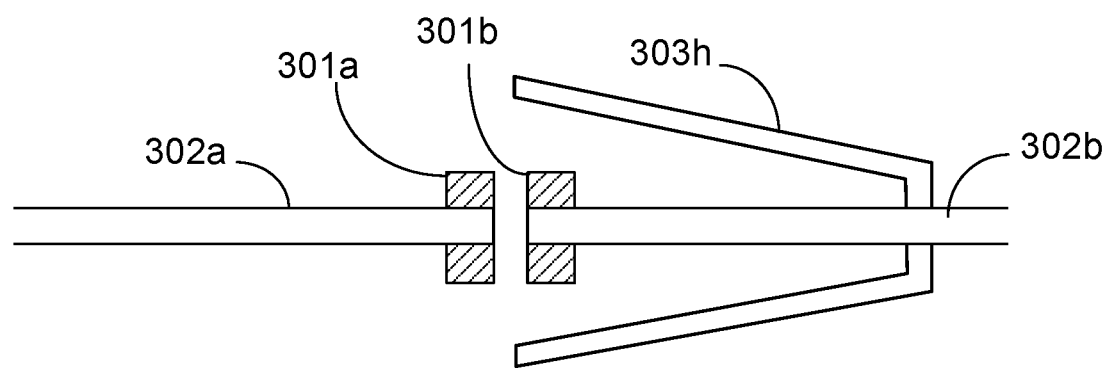

As illustrated in FIGS. 3G and 3H, in certain embodiments a straight magnetic spacer 303g is implemented or a tapered spacer 303h configured in an inverted cone shape is implemented with magnetic collars 301a and 301b where the magnetic collars 301a and 301b have the same diameter.

Figure 4A:
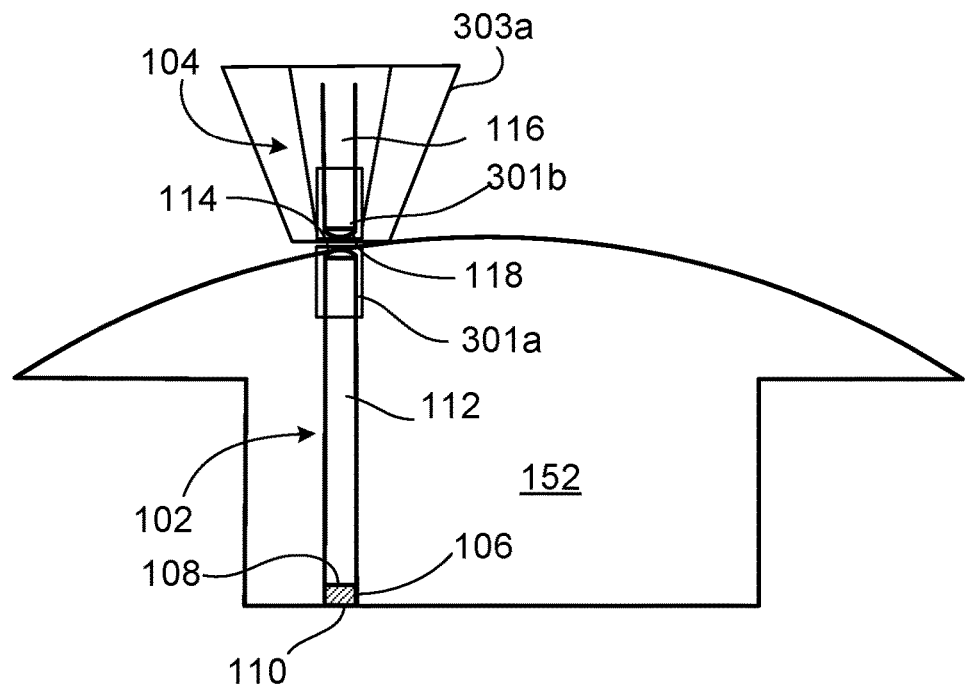
FIG. 4A is an illustration of a keratoprosthesis apparatus implementing an optical fiber system with a pressure sensor.
Figure 4B:
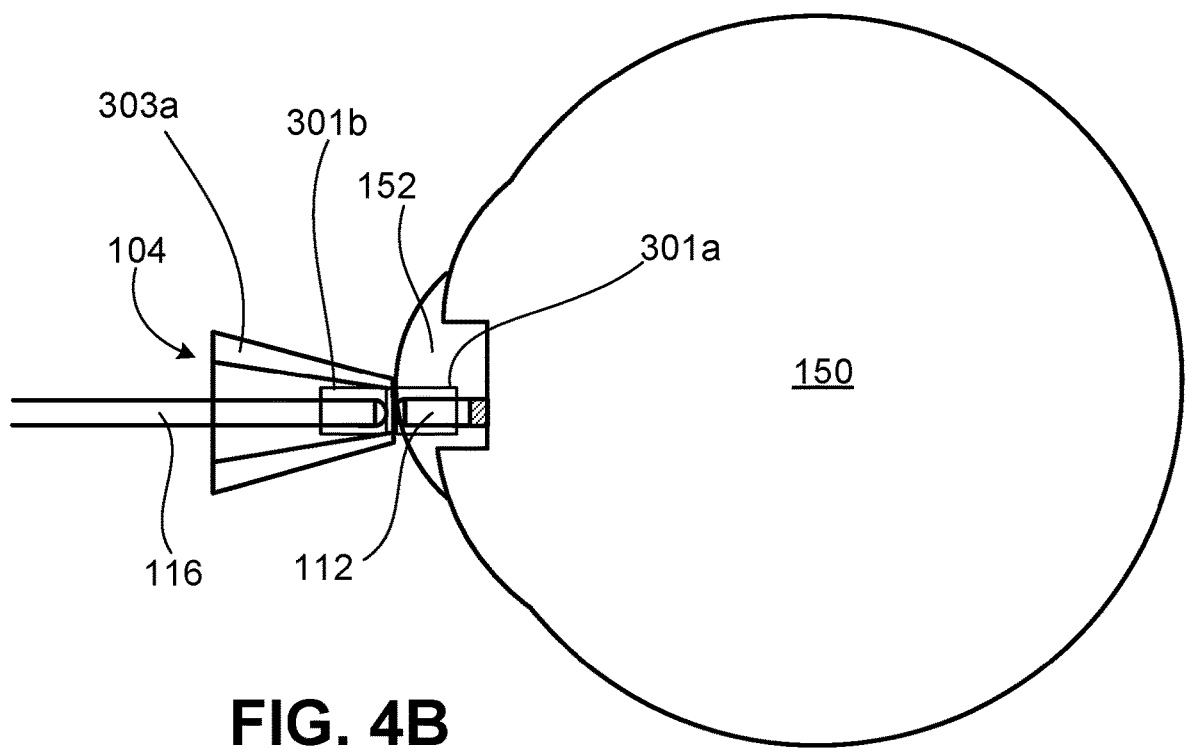
FIG. 4B is an illustration of the keratoprosthesis device of FIG. 4A implanted in an eye.

FIG. 4A is an illustration of a keratoprosthesis apparatus implementing an optical fiber system with a pressure sensor. FIG. 4B is an illustration of the keratoprosthesis device of FIG. 4A implanted in an eye. A device for sensing of intraocular pressure in an eye 150 includes an internal segment 102 that can be integrated into the stem of an artificial cornea 152, such as a Boston Keratoprosthesis (BKPro) artificial cornea and an external segment 104 that is optically coupled to the internal segment 102. The internal segment 102 includes an optical pressure sensor, such as a Fabry-Perot optical cavity 106 (referred to here as an optical cavity 102), that is sensitive to changes in intraocular pressure in the eye 150.

When the internal segment 102 of the device is integrated into the artificial cornea 152 implanted in the eye 150, a deformable surface 110 is in contact with the aqueous humor in the anterior chamber of the eye 150. Intraocular pressure causes the aqueous humor within the eye 150 to exert a pressure on the deformable surface 110, deflecting the deformable surface 110 inwards towards the interior of the optical cavity 106. The degree of deformation of the deformable surface 110 is proportional to the intraocular pressure (within a specified range, such as a range of expected intraocular pressures). Deformation of the deformable surface 110 causes a change in the distance between the deformable surface 110 and the fixed surface 108, thus changing the length of the optical cavity 106 and causing a shift in the resonance frequency of light within the optical cavity 106. The resonance frequency of light within the optical cavity 106 is thus an indication of the intraocular pressure.

To interrogate the resonance frequency of light within the optical cavity 106, the optical cavity 106 is externally illuminated with multiple wavelengths of light and the wavelength that causes resonance within the optical cavity 106 is determined. Light can be transferred from an external light source (not shown) to the optical cavity 106 by a short fiber optic waveguide 112 optically coupled to the optical cavity 106. The fiber optic waveguide 112 can be integrated into the stem of the artificial cornea. The distal end 114 of the fiber optic waveguide 112 can have a polished end that terminates on the anterior surface of the stem of the artificial cornea (e.g., the curved lens of a BKPro artificial cornea). The polished distal end 114 can be a flat surface, an angled surface, a convex surface, a concave surface, or another type of surface that acts as a micro-lens. In some examples, aberration correction can be employed using aspheric lens design.

Interrogation of the intraocular pressure is performed by illuminating the fiber optic waveguide 112 by a light source (not shown) external to the eye. The light source can be a polychromatic light source or a frequency shifting monochromatic light source, such as a light emitting diode (LED), a laser, or another type of narrow- or broad-band light source. Light from the light source can be delivered to the fiber optic waveguide 112 via a long external fiber optic 116 that is positioned external to the eye. The external fiber optic 116 can have a polished proximal end 118, such as a flat surface, an angled surface, a convex surface, a concave surface, or another type of surface that acts as a micro-lens. In some examples, aberration correction can be employed using aspheric lens design. The external fiber optic 116 can be positioned substantially vertically, external to the eye, and with the polished proximal end 118 in close proximity to the polished distal end 1 14 of the fiber optic waveguide 112. The polished proximal end 1 18 of the external fiber optic 116 is coupled via a non-contact coupling system comprising magnetic collars 301a and 301b and spacer 303a. Magnetic collar 301a is connected to the polished distal end 114 of the fiber optic waveguide 112 such that the light can be focused from the external fiber optic 116 into the fiber optic waveguide 112. Spacer 303a permits the magnetic field of magnetic collars 301a and 301b to be close enough to engage one another and align the fiber optic waveguides 112 and 116, while maintaining a gap between polished distal ends 114 and 118.

In certain embodiments, one micro magnet can be embedded in the stem of the keratoprosthesis, while the second magnet is on the interrogation fiber optic cable that is mounted on a slit lamp. Alignment of the interrogation fiber with the intra-ocular pressure KPro sensor can then be performed by moving the interrogation fiber close enough to the Kpro via the slit-lamp.

The apparatuses, systems, and methods may be applied to fiber optic communication of any sort. In some implementations, the methods are employed to facilitate the medical use of μOCT. Implementations disclosed can also be applied to home appliances and other short of communication devices that can implement non-contact coupling of light.

Other Embodiments

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

The orientation of various elements may differ according to other exemplary implementations, and such variations are encompassed by the present disclosure. Features of the disclosed implementations can be incorporated into other disclosed implementations.

While various inventive implementations have been described and illustrated herein, a variety of other means and/or structures for performing the function and/or obtaining the results and/or one or more of the advantages described herein are, and each of such variations and/or modifications is, deemed to be within the scope of the inventive implementations described herein. The foregoing implementations are presented by way of example only and that, within the scope of the appended claims and equivalents thereto, inventive implementations may be practiced otherwise than as specifically described and claimed. Inventive implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way. Accordingly, implementations may be constructed in which acts are performed in an order different than illustrated, which may include performing some acts simultaneously, even though shown as sequential acts in illustrative implementations.

The claims should not be read as limited to the described order or elements unless stated to that effect. It should be understood that various changes in form and detail may be made by one of ordinary skill in the art without departing from the spirit and scope of the appended claims. All implementations that come within the spirit and scope of the following claims and equivalents thereto are claimed.

What is claimed is:

1. An optical fiber coupling system comprising:
a first optical fiber comprising a first magnetic collar attached coaxially to a proximal end of the first optical fiber;
a second optical fiber comprising a second magnetic collar attached coaxially to a proximal end of the second optical fiber, wherein the second magnetic collar is attached to the proximal end of the second fiber so as to have a polarity at a coupling end of the second magnetic collar adjacent a terminus of the proximal end of the second optical fiber, which polarity is opposite a polarity of a coupling end of the first magnetic collar adjacent to a terminus of the proximal end of the first optical fiber; and a spacer attached to at least one of the first optical fiber and the first magnetic collar, the spacer protruding beyond the first magnetic collar with respect to the proximal end of the first optical fiber so as to be positioned between the coupling end of first magnetic collar and the coupling end of the second magnetic collar upon magnetic engagement of a magnetic field of the coupling end of the first magnetic collar with a magnetic field of the coupling end of the second magnetic collar, wherein the spacer is configured to maintain a gap between the first magnetic collar and the second magnetic collar across which the magnetic fields engage one another, whereby the second magnetic collar abuts the spacer, wherein the spacer is configured to allow an optical signal to pass from the first optical fiber to the second optical fiber.

2. The optical fiber coupling system of claim 1, wherein the spacer comprises an opening through which the optical signal can pass.

3. The optical fiber coupling system of claim 2, wherein the opening has a cross section that is smaller than a cross section of the coupling end of second magnetic collar.

4. The optical fiber coupling system of claim 2, wherein the opening has a cross section that is smaller than a cross section of the coupling end of the first magnetic collar and the coupling end of the second magnetic collar.

5. The optical fiber coupling system of claim 1, wherein the spacer has a tapered cross section.

6. The optical fiber coupling system of claim 1, wherein the spacer is composed of a non-magnetic material.

7. The optical fiber coupling system of claim 1, wherein the spacer is configured as a concentric collar.

8. The optical fiber coupling system of claim 1, wherein the first magnetic collar and the second magnetic collar have distinct cross sectional areas at the respective coupling ends.

9. The optical fiber coupling system of claim 1, wherein the spacer includes a recessed region configured for nesting the second magnetic collar.

10. The optical fiber coupling system of claim 1, wherein the spacer is configured to maintain the gap at a distance in the range of 2-10 microns.

11. The optical fiber coupling system of claim 1, wherein the spacer is configured to coaxially align the coupling end of the first magnetic collar with the coupling end of the second magnetic collar.

12. The optical fiber coupling system of claim 1, wherein a distal end of the first optical fiber extends from the first magnetic collar to a light source.

13. The optical fiber coupling system of claim 1, wherein a distal end of the second optical fiber extends from the second magnetic collar to into a keratoprosthesis.

14. The optical fiber coupling system of claim 1, wherein a distal end of the second optical fiber extends from the second magnetic collar into an intraocular lens.

15. The optical fiber coupling system of claim 1, further comprising a pressure sensor positioned on the coupling end of the second magnetic collar.

16. The optical fiber coupling system of claim 1, wherein the respective one of the first optical fiber and the second optical fiber attached to the spacer is configured to move with respect to the spacer.

17. The optical fiber coupling system of claim 16, wherein the respective one of the first optical fiber and the second optical fiber attached to the spacer is configured to rotate with respect to the spacer.

18. A method of coupling optical fibers for communicatively transmitting optical signals, the method comprising:
coaxially attaching a first magnetic collar to a proximal end of a first optical fiber;
coaxially attaching a second magnetic collar to a proximal end of a second optical fiber, wherein the second magnetic collar is attached to the proximal end of the second fiber so as to have a polarity at a coupling end of the second magnetic collar adjacent a terminus of the proximal end of the second optical fiber, which polarity is opposite a polarity of a coupling end of the first magnetic collar adjacent to a terminus of the proximal end of the first optical fiber;
attaching a spacer to at least one of the first optical fiber and the first magnetic collar such that the spacer protrudes beyond the first magnetic collar with respect to the proximal end of the first optical fiber; and
positioning the first magnetic collar with respect to the second magnetic collar so that the spacer is positioned between the coupling end of the first magnetic collar and the coupling end of the second magnetic collar, so that the second magnetic collar abuts the spacer, so that a magnetic field of the coupling end of the second magnetic collar engages a magnetic field of the coupling end of the first magnetic collar, whereby the spacer maintains a gap between the first magnetic collar and the second magnetic collar across which the magnetic fields engage one another, and so that an optical signal is configured to pass from the first optical fiber to the second optical fiber.

19. The method of claim 18, further comprising transmitting the optical signal from the first optical fiber to the second optical fiber through the spacer and across the gap.

20. The method of claim 19, further comprising rotating the first optical fiber with respect to the second optical fiber.

21. The method of claim 19, wherein positioning comprising coaxially aligning the terminus of the first optical fiber with the terminus of the second optical fiber.

22. The method of claim 19, wherein the first optical fiber is positioned with respect to the second optical fiber so that the gap is at a distance in the range of 1 nm-2000 microns.

23. A method of coupling optical fibers for communicatively transmitting optical signals, the method comprising:
coaxially attaching a first magnetic collar to a proximal end of a first optical fiber; coaxially attaching a second magnetic collar to a proximal end of a second optical fiber, wherein the second magnetic collar is attached to the proximal end of the second fiber so as to have a polarity at a coupling end of the second magnetic collar adjacent a terminus of the proximal end of the second optical fiber, which polarity is opposite a polarity of a coupling end of the first magnetic collar adjacent to a terminus of the proximal end of the first optical fiber;
positioning the first magnetic collar with respect to the second magnetic collar so that a gap is between the coupling end of the first magnetic collar and the coupling end of the second magnetic collar, so that a magnetic field of the coupling end of the second magnetic collar engages a magnetic field of the coupling end of the first magnetic collar; and causing an optical signal to be passed from the first optical fiber to the second optical fiber across the gap.

24. The method of claim 23, wherein the first magnetic collar and the first optical fiber are attached to a movable slit lamp, the first optical fiber movable with respect to the slit lamp, the slit lamp configured to move with respect to the second magnetic collar to engage the magnetic field of the coupling end of the second magnetic collar with the magnetic field of the coupling end of the first magnetic collar with the gap positioned therebetween during transmission of the optical signal from the first optical fiber to the second optical fiber.

25. The method of claim 23, wherein the first optical fiber and the second optical fiber are positioned within a chamber comprising a refractive index matching liquid.

26. The method of claim 23, further comprising rotating at least one of the first optical fiber and the second optical fiber in the chamber.

* * * * *